United States Patent [19]

Matsumoto et al.

[11] Patent Number: 5,252,925
[45] Date of Patent: Oct. 12, 1993

[54] DETECTOR ASSEMBLY FOR AN ELECTROMAGNETIC INDUCTION-TYPE CONDUCTIVITY METER

[75] Inventors: Hiroo Matsumoto; Shigeyuki Akiyama, both of Kyoto, Japan

[73] Assignee: Horiba, Ltd., Kyoto, Japan

[21] Appl. No.: 781,712

[22] Filed: Oct. 22, 1991

[30] Foreign Application Priority Data

Oct. 22, 1990 [JP] Japan .................. 2-285098

[51] Int. Cl.⁵ ................. G01R 27/26; G01N 27/06
[52] U.S. Cl. ................... 324/445; 324/450; 324/204; 324/239; 324/693
[58] Field of Search ......... 324/439, 445, 450, 204, 324/693, 724, 219, 220, 239

[56] References Cited

U.S. PATENT DOCUMENTS

| | | | |
|---|---|---|---|
| 3,151,293 | 9/1964 | Blake et al. | 324/445 |
| 3,292,077 | 12/1966 | Sloughter | 324/204 |
| 3,404,336 | 10/1968 | Rosenthal | 324/445 |
| 4,138,639 | 2/1979 | Hutchins | 324/445 |
| 4,860,574 | 8/1989 | Maeda et al. | 324/204 |
| 5,077,525 | 12/1991 | West et al. | 324/204 |
| 5,089,781 | 2/1992 | Arichika et al. | 324/445 |

FOREIGN PATENT DOCUMENTS

| | | | |
|---|---|---|---|
| 0157119 | 9/1982 | Japan | 324/204 |
| 0659944 | 4/1979 | U.S.S.R. | 324/445 |

*Primary Examiner*—Kenneth A. Wieder
*Assistant Examiner*—Glenn W. Brown
*Attorney, Agent, or Firm*—Price, Gess & Ubell

[57] ABSTRACT

An improved detector assembly with an electromagnetic induction-type conductivity meter is provided with a pair of housing members forming a first liquid sample flow path at a central location, and a second liquid sample flow path on their outer circumference. An excitation coil and a detection coil extend about the first liquid sample path, while the second liquid sample flow path interconnects with the first liquid sample flow path both upstream and downstream of the respective coils. The second liquid sample flow path can substantially extend about the coils so that a relatively large induction current can be generated and measured as representative of the liquid sample.

17 Claims, 3 Drawing Sheets

DETECTOR ASSEMBLY FOR AN ELECTROMAGNETIC INDUCTION-TYPE CONDUCTIVITY METER

BACKGROUND OF THE INVENTION

1. Field of the Invention

The present invention relates to a detector assembly or detector block that can be installed as the sensing element in an electromagnetic induction-type conductivity meter wherein electrical current is caused to pass through a liquid sample by an electromagnetic induction and detected by a detector coil to measure the conductivity of a sample. More particularly, the invention relates to a relatively compact and self-contained detector assembly for accomplishing such a measurement.

2. Description of Related Art

It has been known to utilize an immersion-type conductivity meter wherein the actual detector element or sensor can be immersed in the liquid sample within a liquid tank and/or a reaction tank. It has also been known to use a flow-through-type conductivity meter for connection to a pipeline in which a liquid sample passes. In such meters, a detector element is usually mounted in such a manner that the sample may flow through the detector element. These types of meters have been generically known as electromagnetic induction-type conductivity meters.

Generally, electromagnetic induction-type conductivity meters, such as those described above, are relatively large in size and can cause problems in their specific applications. Particularly in the immersion-type conductivity meter, it is frequently necessary to increase the total length of the meter and to adjust that total length, depending upon the level of liquid surface within which the detector element is immersed, particularly in large-size liquid tanks. With regard to the flow-through-type conductivity meters, there is usually a requirement for providing a flange and a holder for mounting the detector element at a midway position relative to the pipeline. Such additional features can significantly increase the cost of the meter.

An additional problem frequently occurs in both the immersion-type conductivity meters and the flow-through-type conductivity meters in that an excitation coil and a detection coil are utilized as the active portions of the detector element, and they are coated within a thin-walled resin or the like to protect it from the sample fluid. These coatings can cause a problem in increasing the difficulty in manufacturing the meters, and can cause a possible problem of liquid leakage if improperly prepared.

Accordingly, there is a demand in the prior art to provide a highly efficient and compact electromagnetic induction-type conductivity meter.

SUMMARY OF THE INVENTION

The present invention has been designed to address the problems mentioned above by providing a detector assembly or block element which is not only small and compact in size, but can be superior in durability and in applications to facilitate an easy sampling in an electromagnetic induction-type conductivity meter. A detector block or assembly is bifurcated and can comprise a pair of plastic resin housing shells or components that can be efficiently manufactured by an injection molding process. A conical cavity in one housing can receive the respective excitation coil and detection coil which, in turn, can be sealed against the other housing half. A sample flow path can extend axially through each of the housing halves, and can also provide circumferential passageways about the other side of the excitation coil and detection transformer. These passageways can define respective U-shaped configurations concentric with the axial passageway, or can be extended circumferentially to have semicircular shapes to increase the flow path for the sample fluid. Such an increased flow path will enable the excitation of a larger sample current.

The respective detector housing shells can be advantageously molded to include male connecting members, for example, for joining with a pipeline. They can also be advantageously molded to enable not only temperature monitoring, but also to provide appropriate integral housing configurations for the excitation coil and detection coil, and also grooves for sealing members.

The housing shells can be formed of an insulating resin and can be of a compact size, and therefore capable of sampling a reduced flow rate. It is also possible for this construction to provide ports that can be utilized for a sampling piping and a periodic calibration with a calibrating liquid, if so desired.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

DESCRIPTION OF THE PREFERRED EMBODIMENTS

The following description is provided to enable any person skilled in the measuring art to make and use the invention and sets forth the best modes contemplated by the inventors of carrying out their invention. Various modifications, however, will remain readily apparent to those skilled in the art, since the generic principles of the present invention have been defined herein specifically to provide an improved compact detector assembly for a conductivity meter.

Referring to the preferred embodiment of FIGS. 1 through 3 and 6, a detector assembly block A for an electromagnetic induction-type conductivity meter is disclosed. The other component elements for processing the detected signal and for driving the excitation coil are only shown schematically in FIG. 3, but are well known in the art. Detector housing members 1 and 2 can be injection molded from a plastic resin material having superior insulation and corrosion resistance characteristics such as a hard vinyl chloride, polypropylene, polyvinylidene fluoride, and Teflon ™.

Figure 6:
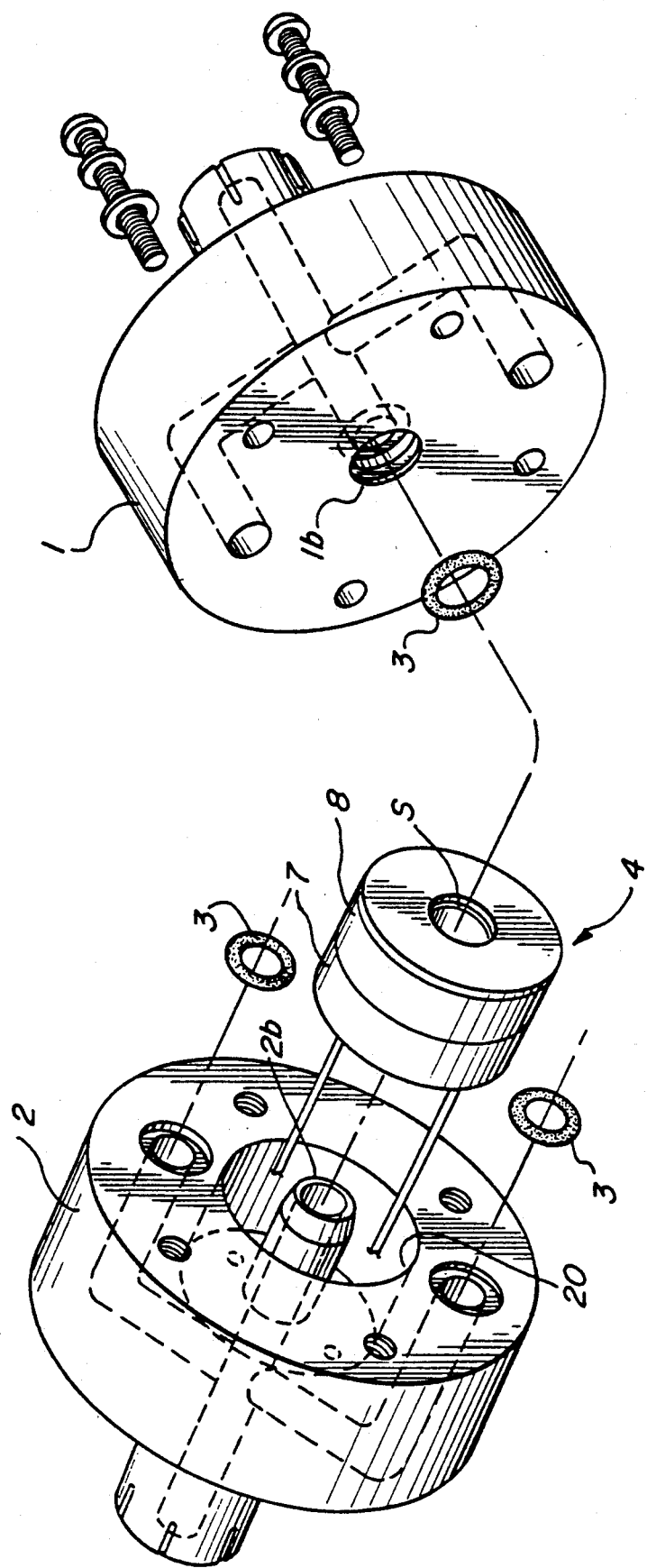
FIG. 6 is an exploded perspective view of the embodiment of FIGS. 1 through 3.

Housing member 1 has a central female concave portion 1b dimensioned to receive a male convex portion 2b, to form a portion of an axial hollow fluid path. The interface surface between the respective housing members 1 and 2 is relatively flat, as shown in FIG. 6, with a central axial flow path or through hole c. This through hole c forms a sample passageway B when the respective housing members 1 and 2 are fastened together by a series of four screw members "a" proportionally placed about the respective housing members to secure them together. Prior to joining these two housing members, a circular detector element 4 is positioned about the central passageway B to be fitted within the cylindrical cavity or indent 20 that surrounds the male convex portion 2b. Mounted within this cavity 20 in housing member or central hollow protrusion 2b is an excitation coil 7 and a detection coil 8 comprising, respectively, a circular iron core and a helical coil wound around the iron core. Each of these coils is housed, respectively, in a metallic case 5 and 6. The respective metallic cases 5 and 6 help isolate each of the coils from interference and openings S adjacent the cylindrical housing wall surrounding the passageway B assist in enabling the measurements by ensuring a flux path to the sample passageway B.

Figure 1:
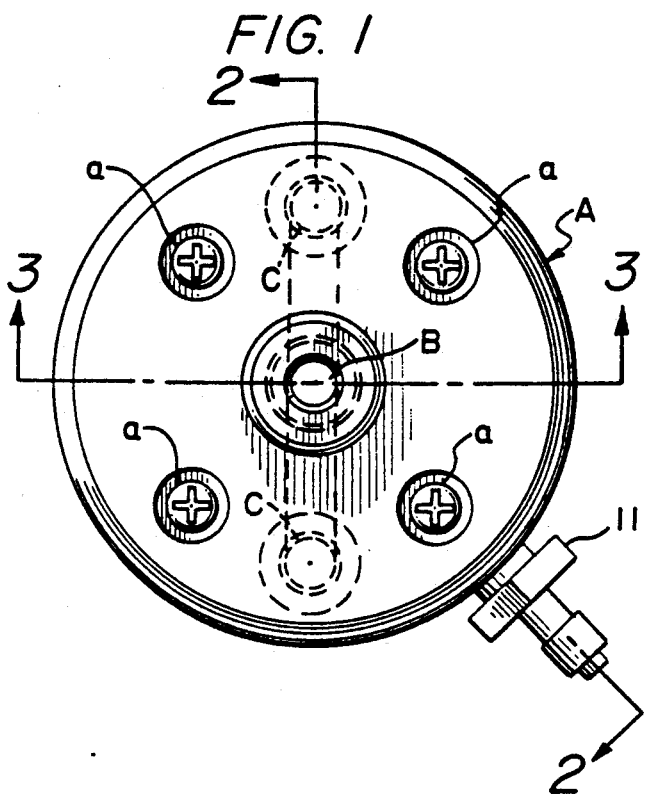
FIG. 1 is a top plan view showing a detector block or assembly of an electromagnetic induction-type conductivity meter.
Figure 2:
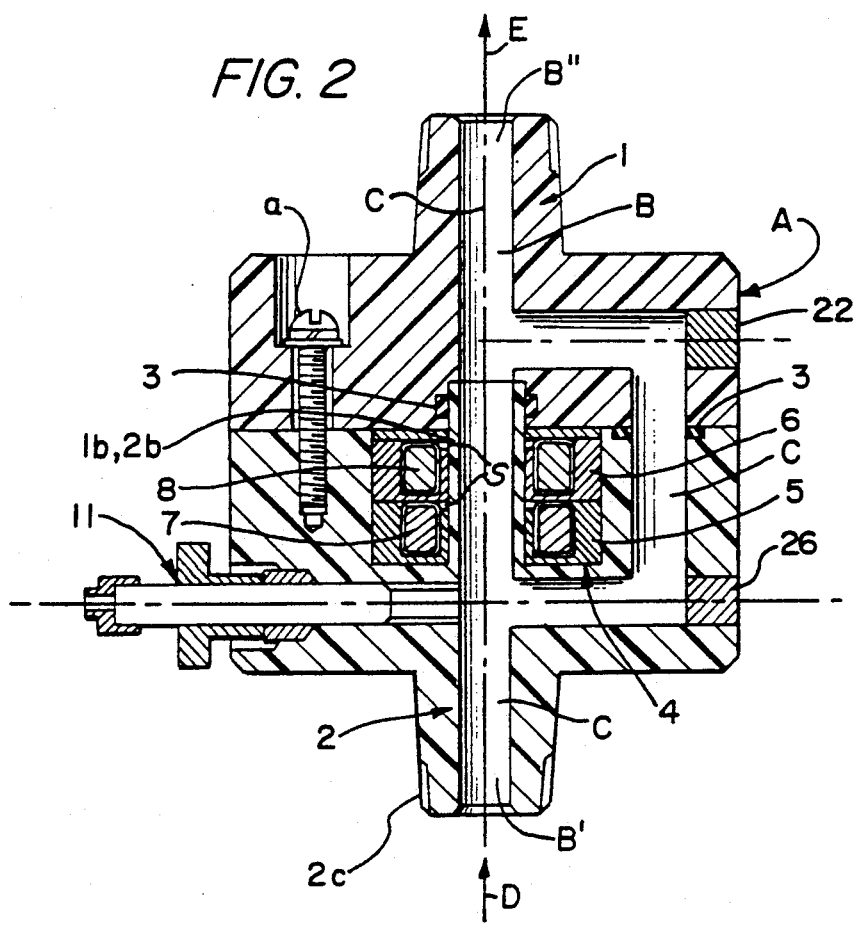
FIG. 2 is a longitudinal sectional view of FIG. 1 taken along the section line I—I thereof shown in FIG. 1.

Reviewing FIG. 2, each of the housing members 1 and 2 is provided with a central passageway B to form a principal sample passageway, and branch passageways or channels having a respective U-shaped configuration on each side of the sample passageway B. B' designates an inflow port for a sample, and B" designates an outflow port for a sample. These outer circumferential sample passageways C communicate with the central passageway B in the vicinity of the inflow port B' and the outflow port B".

Various sealing O-rings 3 can be positioned between the respective housing members 1 and 2 at the interface between the respective housing members, as shown in FIG. 2. This ensures an appropriate isolation of the respective excitation coil 7 and detection coil 8 from the fluid sample. As can be seen adjacent the inflow port B', a series of flutes or grooves 2c is provided on a hollow male coupling member, while adjacent the outflow port B", a similar series of flutes or grooves 1c is provided on another hollow male coupling member so that they can act as appropriate coupling projections if, for example, the detector member A is connected midway between a pipeline (not shown) through which a liquid sample is to travel.

Figure 3:
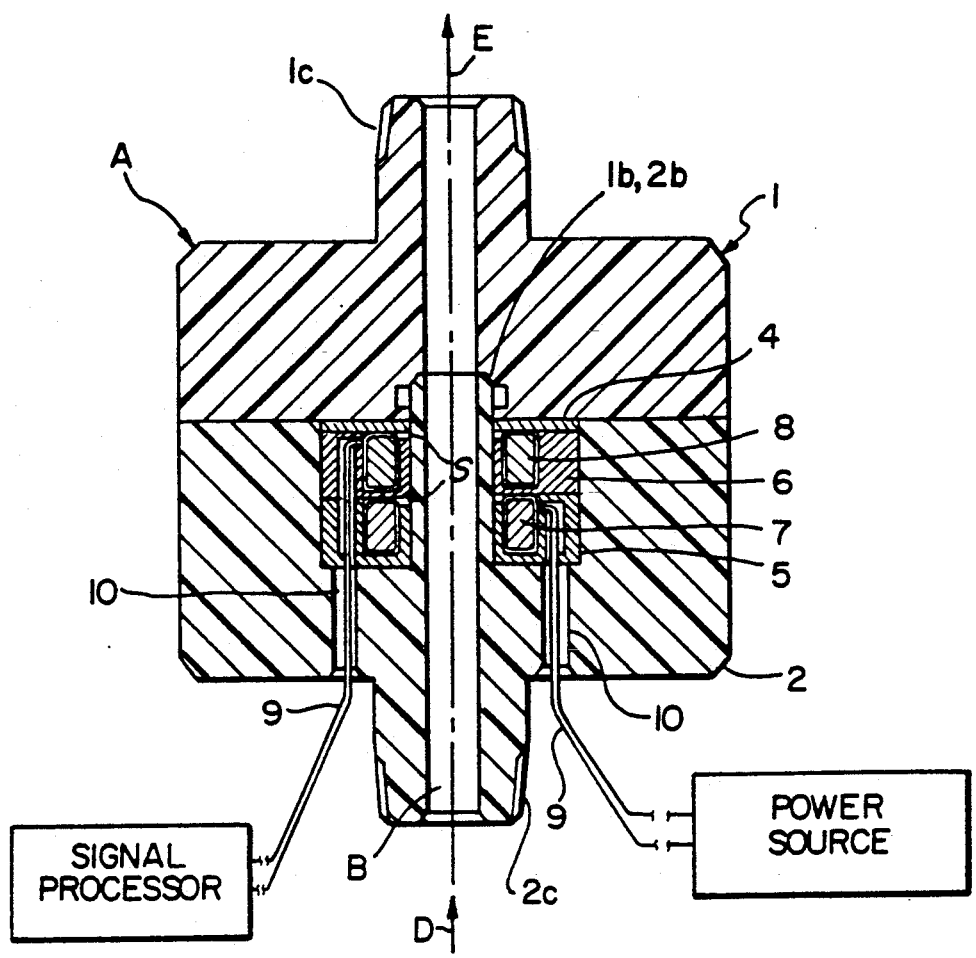
FIG. 3 is another longitudinal sectional view of FIG. 1 taken along the section line II—II shown in FIG. 1.

Referring to FIG. 3, appropriate small holes or apertures 10 can be provided to permit lead wire connections 9 to, respectively, the excitation coil 7 and the detection coil 8. Thus, a power source can be connected to the excitation coil 7, and an analytical portion or meter signal processing circuit can be connected to receive the sampling signal from the detection coil 8.

Referring to FIG. 2, the housing member 2 can be further provided with a temperature sensor 11 through a radial channel that extends outward to a side surface of the housing member 1. When the temperature sensor 11 is appropriately mounted, its sensor element will face and communicate with the sample passageway B. Thus, a highly accurate measurement of conductivity can be achieved by measuring the temperature of the sample and carrying out appropriate calibration operations, as known in the art, to take into account any temperature change of the sample.

As can be appreciated, the temperature sensor 11 is not specifically required, for example, in a case where the sample itself is held at an appointed constant temperature, or is relatively temperature insensitive, or is controlled by means of a thermostat and the like.

The respective housing members 1 and 2 can be readily manufactured through an injection molding process with a selected plastic resin. The assembling of the detector can be accomplished relatively easily by first mounting the respective excitation coil 7 and the detection coil 8 with their lead lines positioned in the appropriate apertures 10. The O-ring seals 3 are then appropriately positioned about a groove in the convex aperture 16 and the annular grooves on the planar surface about the circumferential passageways C. Respective housing members 1 and 2 are then mated, and the screws 4 can connect the housing members together. The temperature sensor 11 can be appropriately mounted in a port on the side of housing member 2.

In operation, a detector block A can be mounted, for example, midway in a pipeline (not shown) through the coupling projections 1c and 2c, to enable a liquid sample to flow through the pipeline in a direction shown by arrow D through the inlet port B' of the detector block A. The liquid sample will be branched between the central sample passageway B and the respective outer circumferential passageways C so that the liquid sample will flow through a central portion axially aligned with the excitation coil 7 and the detection coil 8 about the convex member 2b. The liquid sample will also flow around and on the side of the respective coils through the outer circumferential passageway C, which are positioned 180 degrees with regard to each other. When the excitation coil 7 is appropriately activated, it will generate an induction current, which corresponds to the conductivity of the electrolytes in the sample. This induction current can then be detected by the generated current produced by the detection coil 8, whereby a measurement of the conductivity of the sample can occur. This signal can be appropriately compensated for if any changes occur in the temperature as measured by the temperature sensor 11. As can be determined, the liquid sample from both the central passageway B and the outer circumferential passageways C again join together and exit in the direction of arrow E through the outflow port B" as shown in FIG. 2.

Figure 4:
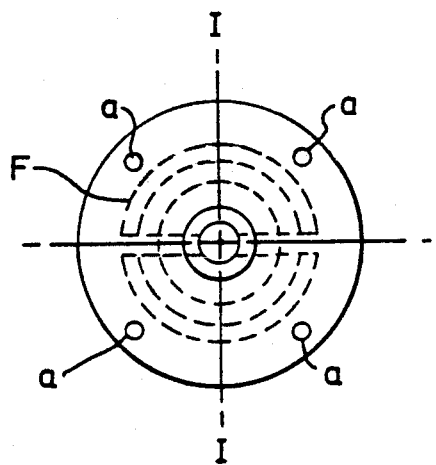
FIG. 4 is a top plan view of an alternative detector block.
Figure 5:
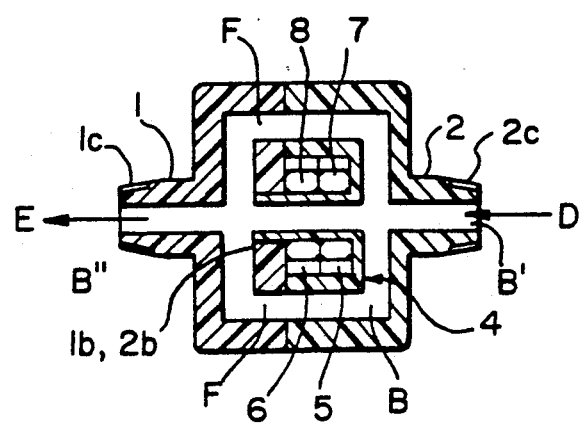
FIG. 5 is a longitudinal sectional view of FIG. 4 taken along the sectional line I—I thereof.

An alternative embodiment of the present invention is disclosed in FIGS. 4 and 5, and can constitute approximately the same construction as shown in the first embodiment. A significant difference, however, can be realized in that the outer circumferential passageway F in the respective housing members 1 and 2 is enlarged into almost a semicircular shape, as shown in FIG. 4. As a result, the outer circumferential passageway F forms almost the entire outer circumferential area of the detector element, and an induction current that is generated by the excitation coil 7 will extend over almost the entire circumference so that the detection coil 8 will be addressed with a much larger signal than could be attained by virtue of only the constant circumferential cross-sectional passageway shown in the embodiment of FIGS. 1 to 3.

A larger measurement signal will help stabilize the measurement process, and can increase the accuracy of detection. As can be readily appreciated, the modifications required to create the embodiment shown in FIGS. 4 and 5 from that of the present invention of FIGS. 1 through 3 and 6 are within the skill of a person in this field, and such a construction can also be formed with injection molded plastic parts.

In either form of the present invention, the detector element A can consist of a relatively simple block member formed of a pair of plastic housing members that can be efficiently manufactured and assembled. The detector element A will not only be durable, but will be relatively free from any leakage problem. The detector element A can be manufactured to be of a relatively compact small size for use in applications wherein sampling is desired with a relatively reduced sample flow rate. While not shown, sampling piping and a periodic calibration with a calibrating liquid can also be easily accomplished through connections with ports that are shown with plugs 22 and 26 in FIG. 2.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. An improved detector assembly of an electromagnetic induction-type conductivity meter comprising:
    a plastic material housing member having a first liquid sample flow path extending therethrough, the housing member being bifurcated into a first component and a second component, the first component having a central hollow protrusion forming a portion of the first liquid sample flow path, and the second component having a through passage with a cavity for receiving the central hollow protrusion;
    an excitation coil extending about the first liquid sample flow path;
    a detection coil extending about the first liquid sample flow path, and
    means for providing a second liquid sample flow path that interconnects with the first liquid sample flow path both upstream and downstream of the respective coils, whereby the excitation coil enables an induction current to be generated in the liquid sample and the detection coil measures the induction current as representative of the conductivity of the liquid sample.

2. The invention of claim 1, wherein the second flow path includes a first channel and a second channel that are approximately 180 degrees apart.

3. The invention of claim 1, wherein the second flow path substantially surrounds the respective coils and the first liquid sample flow path.

4. The invention of claim 1 wherein the plastic material is selected from vinyl chloride, polypropylene, polyvinylidene fluoride, and Teflon ™.

5. The invention of claim 1, further including means for sensing the temperature of the first liquid sample flow path mounted on the housing member.

6. The invention of claim 1, wherein the central hollow protrusion is encompassed with an indent of a configuration to support the respective transformers.

7. The invention of claim 6, further including a respective hollow male coupling member on each component.

8. An improved detector assembly of an electromagnetic induction-type conductivity meter comprising:
    a housing member having a first liquid sample flow path extending therethrough;
    an excitation coil extending about the first liquid sample flow path;
    a detection coil extending about the first liquid sample flow path, and
    means for providing a second liquid sample flow path that interconnects with the first liquid sample flow path both upstream and downstream of the respective coils and substantially surrounds the respective coils and the first liquid sample flow path, the second liquid sample flow path being adjacent the coils, whereby the excitation coil enables an induction current to be generated in the liquid sample and the detection coil measures the induction current as representative of the conductivity of the liquid sample.

9. An improved detector assembly of an electromagnetic induction-type conductivity meter comprising:
    a housing member having a first liquid sample flow path extending therethrough;
    an excitation coil extending about the first liquid sample flow path;
    a detection coil extending about the first liquid sample flow path, and
    means for providing a second liquid sample flow path that interconnects with the first liquid sample flow path both upstream and downstream of the respective coils, the second liquid sample flow path being adjacent the coils and substantially surrounding the coils, whereby the excitation coil enables an induction current to be generated in the liquid sample and the detection coil measures the induction current as representative of the conductivity of the liquid sample.

10. The invention of claim 9, wherein the housing member is formed of a plastic material.

11. The invention of claim 10, wherein the housing member is bifurcated into a first component and a second component, the first component having a central hollow protrusion forming a portion of the first liquid sample flow path, and the second component having a through passage with a cavity for receiving the central protrusion.

12. The invention of claim 11, wherein the central hollow protrusion is encompassed with an indent of a configuration to support the respective coils.

13. The invention of claim 12, further including a respective hollow male coupling member on each component.

14. The invention of claim 12, wherein the plastic material is selected from vinyl chloride, polypropylene, polyvinylidene fluoride, and Teflon ™.

15. An improved detector assembly of an electromagnetic induction-type conductivity meter connectable to a pipeline, comprising:
    a two-piece molded housing member unitarily connected together and having a first liquid sample flow path extending therethrough including first and second male coupling projections for connection to a pipeline;
    an excitation coil extending about the first liquid sample flow path;
    a detection coil extending about the first liquid sample flow path, and means for providing a second liquid sample flow path extending through the housing member that interconnects with the first liquid sample flow path both upstream and downstream of the respective coils, the second liquid sample flow path including a first channel and a second channel that are approximately 180 degrees apart relative to the first liquid sample flow path, the second liquid sample flow path being adjacent the coils, whereby the excitation coil enables an induction current to be generated in the liquid sample and the detection coil measures the induction current as representative of the conductivity of the liquid sample.

16. The invention of claim 15 wherein the housing member is formed of a plastic material.

17. The invention of claim 15, wherein the housing member is bifurcated into a first component and a second component, the first component having a central hollow protrusion forming a portion of the first liquid sample flow path, and the second component having a through passage with a cavity for receiving the central protrusion.

* * * * *